United States Patent [19]
Fuisz

[11] 3,955,558
[45] May 11, 1976

[54] INSTRUMENT FOR SPINAL TAPS

[75] Inventor: Richard C. Fuisz, New York, N.Y.

[73] Assignee: Medcom, Inc., New York, N.Y.

[22] Filed: Nov. 4, 1974

[21] Appl. No.: 520,320

[52] U.S. Cl. ................................ 128/2 B; 128/221
[51] Int. Cl.² ............................................. A61B 5/00
[58] Field of Search .......... 128/2 B, 2 M, 215, 221,
128/303 B, 303 R, 305, 305.1, 305.3, 310,
314, 347, DIG. 6; 27/24 R, 24 A

[56] References Cited
UNITED STATES PATENTS

| | | | |
|---|---|---|---|
| 2,238,323 | 4/1941 | Hollingsworth ..................... | 128/215 |
| 2,245,350 | 6/1941 | Marshall ........................... | 128/215 X |
| 2,590,895 | 4/1952 | Scarpellino ........................ | 128/221 |
| 2,705,949 | 4/1955 | Silverman .......................... | 128/2 B |
| 2,830,587 | 4/1958 | Everett ............................. | 128/221 |
| 2,952,256 | 9/1960 | Meader et al ...................... | 128/221 |
| 3,021,842 | 2/1962 | Flood ............................... | 128/215 |
| 3,053,256 | 9/1962 | Cooper et al ...................... | 128/215 X |
| 3,090,384 | 5/1963 | Baldwin et al ..................... | 128/221 |
| 3,477,423 | 11/1969 | Griffith ............................. | 128/2 B |
| 3,788,119 | 1/1974 | Arrigo ............................. | 128/221 X |

FOREIGN PATENTS OR APPLICATIONS

| | | | |
|---|---|---|---|
| 770,998 | 9/1934 | France ............................. | 128/215 |

*Primary Examiner*—John D. Yasko
*Attorney, Agent, or Firm*—Wolder & Gross

[57] ABSTRACT

An instrument for performing a spinal tap includes a body member carrying a hypodermic needle of non-circular transverse cross section and a sharply beveled tip. A guide block has an obliquely extending complementary non-circular bore which is axially slideably engageable by the needle to maintain its orientation and prevent its axial rotation. In puncturing the spinal column, the needle is guided by the block bore and upon entry, cuts a flap in the spinal column surrounding tissue which flap closes the needle entry opening upon withdrawal of the needle.

5 Claims, 9 Drawing Figures

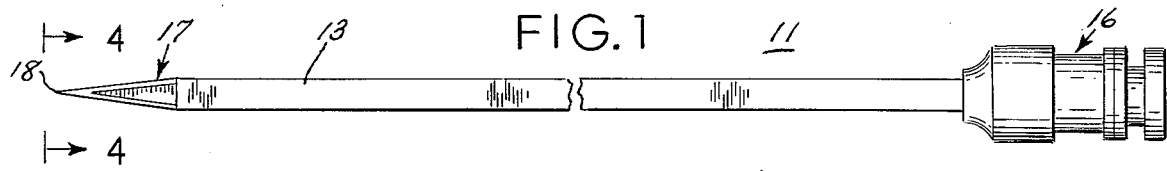
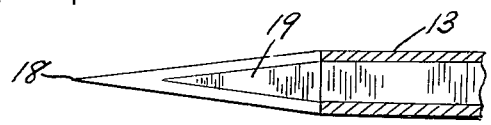
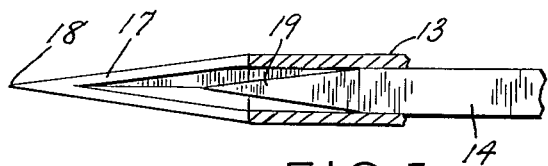
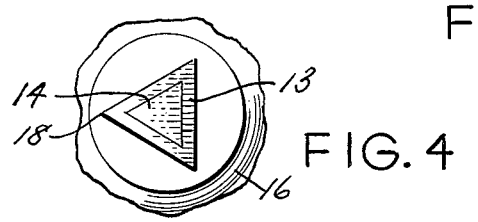
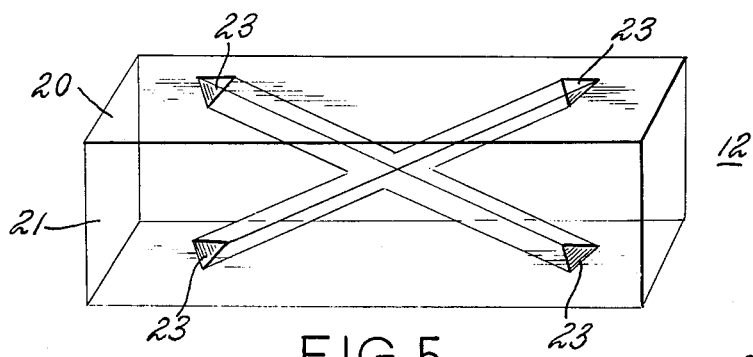
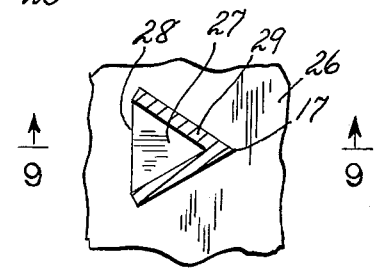
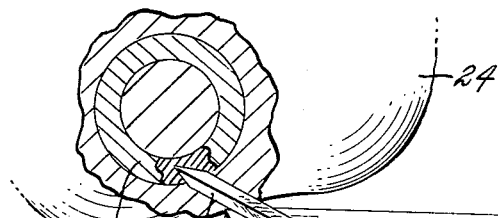
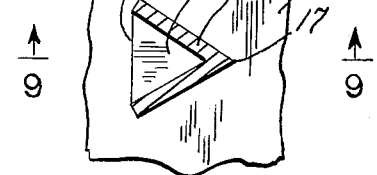
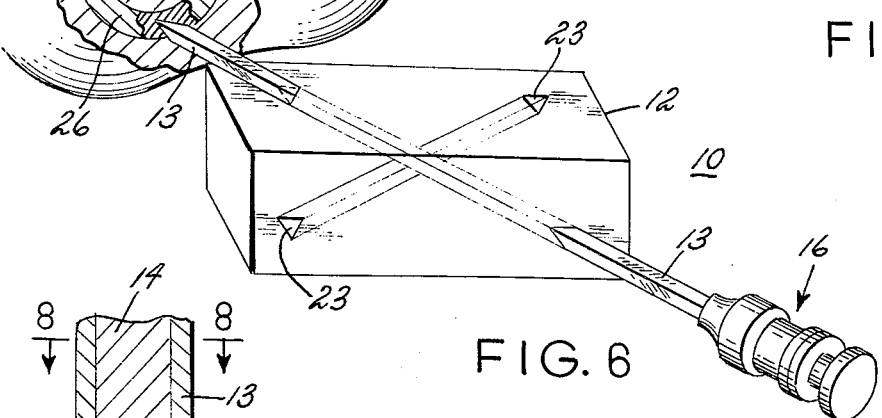
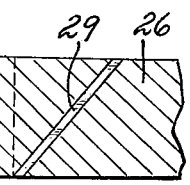

INSTRUMENT FOR SPINAL TAPS

BACKGROUND OF THE INVENTION

The present invention relates generally to improvements in surgical procedures and it relates particularly to an improved device for performing spinal taps.

Among the surgical procedures which require a spinal puncture, that is, the introduction of a needle into the subarachnoid space, is a spinal tap for obtaining spinal fluid for analysis or for relieving the spinal fluid pressure. In performing the spinal tap in the conventional manner, after suitable preparation, a bevelled needle is inserted between a lumbar interspace, usually the fourth lumbar interspace and after it enters the subarachnoid space as evidenced by the sudden release of the resistance of the dura, the stylet is withdrawn and the spinal fluid collected. The conventional spine tapping procedures and the instruments employed, possess numerous drawbacks and disadvantages and an important consequence of these are the undesirable after effects of a spinal tap, such as bad headaches and the like. These are believed to be the consequence of the leaking of spinal fluid from the punctured outer or sheath tissue of the spinal column, which is very frequently caused by the coring of this tissue produced by the insertion of the needle, or by the bevel of the needle being turned in such a manner as to cause an ineffective valve in the dura and allow excess leakage.

It is a principal object of the present invention to provide an improved surgical device.

Another object of the present invention is to provide an improved device for performing a spinal puncture in effecting fluid access to the subarachnoid space.

Still another object of the present invention is to provide an improved device for performing a spinal tap in which the leakage of spinal fluid following the termination of the tap is prevented or minimized.

Still a further object of the present invention is to provide a device which forces the user to properly insert the spinal needle bevel.

A further object of the present invention is to provide a device of the above nature characterized by its great reliability, ease and convenience of application and use, ruggedness and high versatility and adaptability.

The above and other objects of the present invention will become apparent from a reading of the following description taken in conjunction with the accompanying drawing, which illustrates a preferred embodiment thereof.

In a sense, the present invention contemplates the provision of a surgical device comprising a hypodermic needle having a bevelled distal end and guide means restricting the needle to movement in an axial direction at a predetermined orientation and preventing the rotation of the needle about its longitudinal axis.

In the preferred form of the improved device, the hypodermic needle is of non-circular transverse cross-section, advantageously of equilateral triangular transverse cross-section, and is sharply bevelled at its distal end, so that the tip coincides with an apex of the needle transverse cross-section. The guide means includes a block having an oblique linear bore having a cross-section corresponding to that of the needle, the needle axially slideably engaging and projecting through the bore and being prevented from rotating about the longitudinal axis of the bore. The needle is slideably telescoped by a stylet whose distal face coincides with the plane of the plane of the distal end of the needle, and the needle and stylus are mounted on a manipulatable head member in the known manner.

In performing a spinal puncture with the present improved device, a flap is formed in the spinal column outer tissue in the area of entry of the needle, and the flap returns to a position closing the puncture upon withdrawal of the needle to minimize or prevent leakage of spinal fluid and its undesirable consequence. The device is simple and reliable, easy and convenient to use and of high versatility and adaptability.

BRIEF DESCRIPTION OF THE DRAWINGS

FIG. 1 is a top plan view of the needle portion of a device embodying the present invention;

FIG. 2 is an enlarged fragmentary top plan view of the distal end thereof;

FIG. 3 is a view similar to FIG. 2 illustrating the stylus portion partially retracted;

FIG. 4 is a sectional view taken along line 4—4 in FIG. 1;

FIG. 5 is a front perspective view of the guide member portion of the improved device;

FIG. 6 is a perspective view, partially diagrammatic, of the improved device, illustrating its application in the performance of a spinal puncture;

FIG. 7 is a longitudinal sectional view illustrating the area of insertion of the needle attendant to a spinal puncture;

FIG. 8 is a sectional view taken along line 8—8 in in FIG. 7; and

FIG. 9 is a sectional view taken along line 9—9 of FIG. 8.

DESCRIPTION OF THE PREFERRED EMBODIMENT

Referring now to the drawing which illustrates a preferred embodiment of the present invention, the reference numeral 10 generally designates the improved surgical device which comprises a tap member 11 for performing the actual spinal puncture and a guide member 12 for maintaining the tap member 11 in a preselected proper orientation and for preventing the rotation of the tap member 11 about its longitudinal axis.

The tap member 11, except for the shape of the needle and the stylet, per se, is similar in construction to the conventional instrument for performing a spinal tap and includes a hypodermic needle 13 and a slideably telescoping stylet 14, the hypodermic needle 13 and the stylet 14 being connected to and controlled and manipulated by an enlarged head member 16 mounted at the proximal ends of needle 13 and stylus 14.

The needle 13 is tubular and of the flexibility and gauge of hypodermic needles normally used for spinal puncture, for example 20 to 22 gauge, and, in accordance with the present invention, is of non-circular, specifically equilateral triangular transverse cross-section. The distal end 17 of the needle 13 is beveled, the bevel plane being such that the tip 18 of the needle 13 coincides with an apex of the transverse cross section of the needle.

The stylet 14 slideably matingly telescopes the needle 13 and has a triangular transverse cross-section corresponding to that of the bore of the needle 13. The distal end 19 of the stylus 14 is beveled along a plane which coincides with the bevel plane of the needle 13, so that the beveled faces of needle 13 and stylet 14 are coplanar when the stylet 14 is in its fully advanced position.

The guide member 12 is in the shape of a rectangular block formed of a clear transparent material, such as lucite, plexiglass, polystyrene or the like, and has rectangular top and front faces 20 and 21 respectively. A symmetrically disposed pair of guide bores 23 are formed in the block 12, each of the bores 23 extending obliquely from a respective side of the block front face 21 to the correspondingly opposite side of the block top face 20. Each bore 23 is of a transverse cross-section similar to, but slightly greater than that of the outside of needle 13, so as to longitudinally, slideably receive the needle 23 and prevent the rotation of the needle about its longitudinal axis. The triangular openings in front face 21 to the bores 23 have their upper edges horizontal or parallel to the top and bottom edges of block front face 21.

In employing the improved surgical device 10 described above, the needle 13 with the stylet 14 in its advanced position is inserted through a bore 23, for example, through the front wall right hand opening, and with the subject 24 lying on his side in a proper position with his knees tightly drawn to his abdomen, the tip of the needle is applied to the subject's back in the area of a selected lumbar interspace, for example, the fourth lumbar interspace. The guide member 12 is then advanced into firm engagement with the subject's back with the needle 13 oriented at an angle to the medial front and rear plane of the spinal column, but directed toward the subachranoid space. The guide member 12 is thus firmly held and axial pressure applied to the needle 13 to advance it as guided by bore 23 through the spinal column outer tissue to pass the interspinous ligament and puncture the dura to enter the subachranoid space. As the needle 13 penetrates the spinal column outer tissue 26, it forms a triangular flap 27 therein integrally joined with the outer tissue along one side 28 of the flap, the other converging two sides 29 being slit from the tissue. The flap sides 29 are slit or cut by the corresponding sharp distal end edges of the needle 13 and are bevelled to converge inwardly, the flap 27 being bent inwardly with the insertion of the needle 13. After puncture of the spinal column and entry into the subachranoid space, the stylet 14 is withdrawn and the spinal fluid collected in the known manner.

After the collection of the desired quantity of spinal fluid, the needle 13 is withdrawn and the flap 27, under its own resiliency and the internal spinal fluid pressure returns to a closed position to seal the punctured area of the spinal column outer tissue and prevent any leakage of spinal fluid.

While the invention has been discussed with respect to a spinal tap, it is useful anywhere on the body. For example, it may be used for introcardiac injections, thorocentises, and ordinary intravenous, where the needle may be stabilized by other than tape.

While there have been described and illustrated a preferred embodiment of the present invention, it is apparent that numerous alterations, omissions and additions may be made without departing from the spirit thereof.

I claim:

1. A surgical device comprising a tubular hypodermic needle of triangular transverse cross-section and having a distal end beveled along a plane with the distal tip of said needle coinciding with an apex of the triangular section of said needle, a stylet slideably telescoping said hypodermic needle and guide means for restricting said needle to movement in an axial direction at a predetermined orientation and preventing the rotation of said needle about its longitudinal axis.

2. The surgical device of claim 1, wherein said guide means comprises a guide member having a guide passageway with a transverse cross-section corresponding to that of said needle, said needle slideably engaging and projecting beyond said passageway.

3. The surgical device of claim 1, wherein said stylet is of triangular transverse cross-section and has a distal face coinciding with said bevel plane when said stylet is in its advanced position.

4. The surgical device of claim 1, wherein said guide member comprises a block having an obliquely extending bore therethrough of triangular transverse cross-section defining said passageway.

5. The surgical device of claim 4, wherein said block has a front face and a top face and has a pair of said bores formed therein extending from respective side portions of said front face to opposite side portions of said top face.

* * * * *